(12) United States Patent
Havel

(10) Patent No.: US 9,700,400 B2
(45) Date of Patent: Jul. 11, 2017

(54) ATTACHMENT OF STENT TO GRAFT FABRIC WITH AN ANCHORING MACHINE STITCHING

(71) Applicant: William John Havel, West Lafayette, IN (US)

(72) Inventor: William John Havel, West Lafayette, IN (US)

(73) Assignee: Cook Medical Technology LLC, Bloomington, IN (US)

( * ) Notice: Subject to any disclaimer, the term of this patent is extended or adjusted under 35 U.S.C. 154(b) by 981 days.

(21) Appl. No.: 13/772,009

(22) Filed: Feb. 20, 2013

(65) Prior Publication Data
US 2014/0236280 A1    Aug. 21, 2014

(51) Int. Cl.
*A61F 2/07* (2013.01)
*D05B 21/00* (2006.01)
*A61F 2/82* (2013.01)

(52) U.S. Cl.
CPC ............ *A61F 2/07* (2013.01); *A61F 2/82* (2013.01); *D05B 21/00* (2013.01); *A61F 2002/075* (2013.01); *A61F 2220/0075* (2013.01); *A61F 2240/001* (2013.01)

(58) Field of Classification Search
CPC .............. D05B 21/00; A61F 2002/075; A61F 2220/0075; A61F 2240/001; A61F 2/07; A61F 2/82; A61F 2/04
See application file for complete search history.

(56) References Cited

U.S. PATENT DOCUMENTS

| | | | |
|---|---|---|---|
| 5,897,589 A | 4/1999 | Cottenceau et al. | |
| 6,123,722 A | 9/2000 | Fogarty et al. | |
| 6,192,944 B1 | 2/2001 | Greenhalgh | |
| 6,540,773 B2 | 4/2003 | Dong | |
| 6,878,161 B2* | 4/2005 | Lenker | A61F 2/07 623/1.12 |
| 7,641,681 B2 | 1/2010 | Sherry et al. | |
| 8,209,843 B2 | 7/2012 | Thistle | |
| 2003/0055484 A1 | 3/2003 | Lau et al. | |
| 2005/0102022 A1 | 5/2005 | Solovay et al. | |
| 2005/0159803 A1* | 7/2005 | Lad | A61F 2/07 623/1.13 |
| 2007/0276462 A1 | 11/2007 | Isancea et al. | |
| 2009/0043373 A1 | 2/2009 | Arnault de la Menardiere et al. | |

(Continued)

FOREIGN PATENT DOCUMENTS

| | | |
|---|---|---|
| EP | 2103278 A1 | 9/2009 |
| EP | 2679197 A1 | 1/2014 |

(Continued)

OTHER PUBLICATIONS

European Search Report for corresponding European Application No. 14275027.2 dated Jun. 3, 2014.

(Continued)

*Primary Examiner* — Christopher L Templeton
*Assistant Examiner* — Lucas Paez
(74) *Attorney, Agent, or Firm* — Brinks Gilson & Lione

(57) ABSTRACT

The invention relates to stent-grafts having a continuous anchoring machine stitching and methods of attachment of a stent to the graft material. The continuous anchoring machine stitching includes a series of loop points used to attach the stent to the graft material.

13 Claims, 4 Drawing Sheets

(56) References Cited

U.S. PATENT DOCUMENTS

2009/0149939 A1  6/2009  Godlewski et al.
2011/0071614 A1  3/2011  Majercak et al.

FOREIGN PATENT DOCUMENTS

| WO | WO 99/37242 A1    | 7/1999  |
| WO | WO 00/78250 A1    | 12/2000 |
| WO | WO 03/007848 A2   | 1/2003  |
| WO | WO 2005/112821 A2 | 12/2005 |
| WO | WO 2013/038999 A1 | 3/2013  |

OTHER PUBLICATIONS

Examination report for European Application No. 14275027.2, dated Dec. 8, 2016, 3 pages.

* cited by examiner

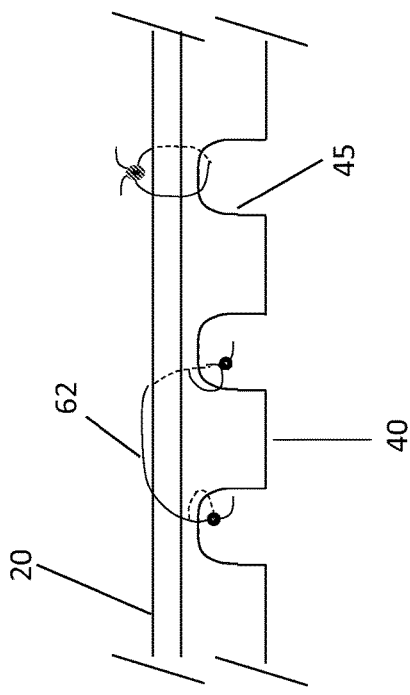
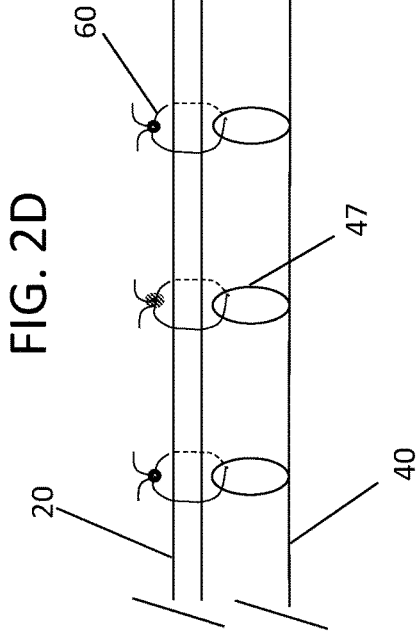
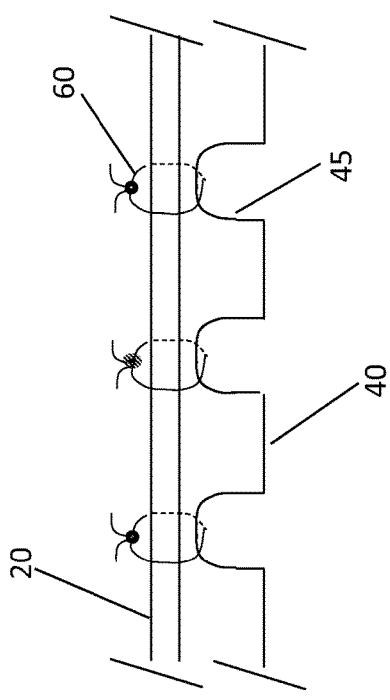
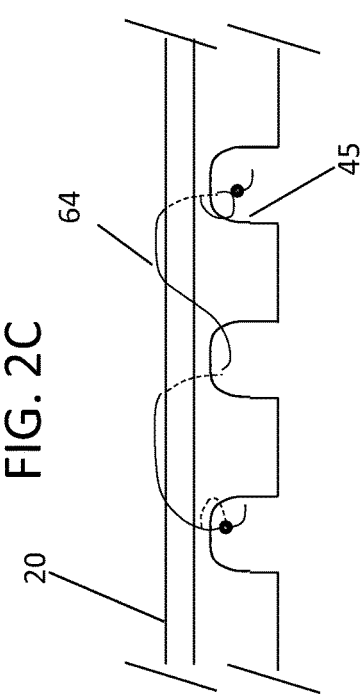

ATTACHMENT OF STENT TO GRAFT FABRIC WITH AN ANCHORING MACHINE STITCHING

TECHNICAL FIELD

The present invention relates generally to stent-grafts with reduced risk of fluid leakage and methods for attaching a stent to a graft.

BACKGROUND OF THE INVENTION

Stents may be inserted into an anatomical vessel or duct for various purposes. Stents may maintain or restore patency in a formerly blocked or constricted passageway, for example, following a balloon angioplasty procedure. Other stents may be used in different procedures in conjunction with a graft material to form a stent-graft, for example, to hold the graft in an open configuration to treat an aneurysm. Additionally, stents coupled to one or both ends of a graft may extend proximally or distally away from the graft to engage a healthy portion of a vessel wall away from a diseased portion of an aneurysm to provide endovascular graft fixation.

Stents may be either self-expanding or balloon-expandable, or they can have characteristics of both types of stents. Self-expanding stents may be delivered to a target site in a compressed configuration and subsequently expanded by removing a delivery sheath, removing trigger wires and/or releasing diameter reducing ties. In a stent made of a shape memory alloy such as nitinol, the shape-memory alloy may be employed to cause the stent to return to a predetermined configuration upon removal of the sheath or other device maintaining the stent in its predeployment configuration.

With balloon-expandable stents, the stent may be delivered and deployed using a catheter having proximal and distal ends and one or more balloons disposed on the catheter. The stent may be coupled to the balloon during insertion until the target site is reached, and then deployed by inflating the balloon to expand the stent to bring the stent into engagement with the target site. Alternatively, the stent may be placed separately in the vessel and a subsequent catheter having an expansion portion may then be inserted into the stent to expand the stent at the target site.

When stents are employed as part of a stent-graft, the stent commonly is attached to the graft using one or more sutures. Typically, the sutures are hand-sewn around the stent and directly through the graft at multiple locations to secure the stent to the graft. Such suturing techniques may be labor intensive. Further, the formation of suture holes in the graft may increase the risks of leakage through the graft, particularly since the size of such suture holes may increase over time.

Current stent-fabric attachment techniques include either tack stitching or a running stitch that follows the stent. At each stitch point, a puncture hole is made in the fabric, one on either side of the stent wire. Having suture holes presents more opportunities for fluid leakage through the graft fabric. Furthermore, cinching the stitch pulls the fabric around the stent. If the fabric is not stretchable, tightening the suture pulls the thread to one side of the puncture hole, opening it up and potentially increasing the risk of leakage.

Another difficulty with current manufacturing techniques is that they require a pattern to be drawn on the graft fabric to indicate where stents are placed during hand stitching of the stents. Drawing or marking has the potential to contaminate or damage graft fabric. Hand-stitching to a pattern also is associated with human error and increased variance in manufacturing tolerances. A method of automating the stitching process would eliminate the need to mark up the fabric and would reduce manufacturing tolerances.

Thus, there is a need for improved techniques and methods for attaching graft material to a stent without the problem of creating holes in the graft fabric and the difficulty with marking up stain-resistant fabrics.

SUMMARY OF THE INVENTION

The present invention relates to stent-grafts having an anchoring machine stitching on the graft materials and methods of manufacture thereof.

One aspect of the invention provides a stent-graft having a stent comprising a wire configured in a stent wire pattern; and graft material, where a continuous anchoring machine stitching is sewn into the graft material. The continuous machine stitching follows the stent wire pattern and includes a plurality of loop points. The plurality of loop points substantially outlines the stent wire pattern and the stent wire is attached to the graft material at the plurality of loop points.

Another aspect of the invention provides a method of manufacturing a stent-graft. The method involves sewing a continuous anchoring machine stitching, with loop points, onto the graft material; forming the graft material into a desired shape for the stent-graft; aligning the machine stitching with a wire of a stent; and attaching the stent to the graft at the loop points.

Other systems, methods, features and advantages of the invention will be apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIGS. 2A-2E are close-up views of several exemplary embodiments showing the attachment of a stent strut to the graft material at the loop points of the anchoring machine stitching.

DETAILED DESCRIPTION

Although the structures and methods of the present invention will be generally described with reference to simple tubular prostheses having a single lumen, it will be understood that the structures and methods of the present invention also encompass more complex branching endoluminal prostheses.

Figure 1:
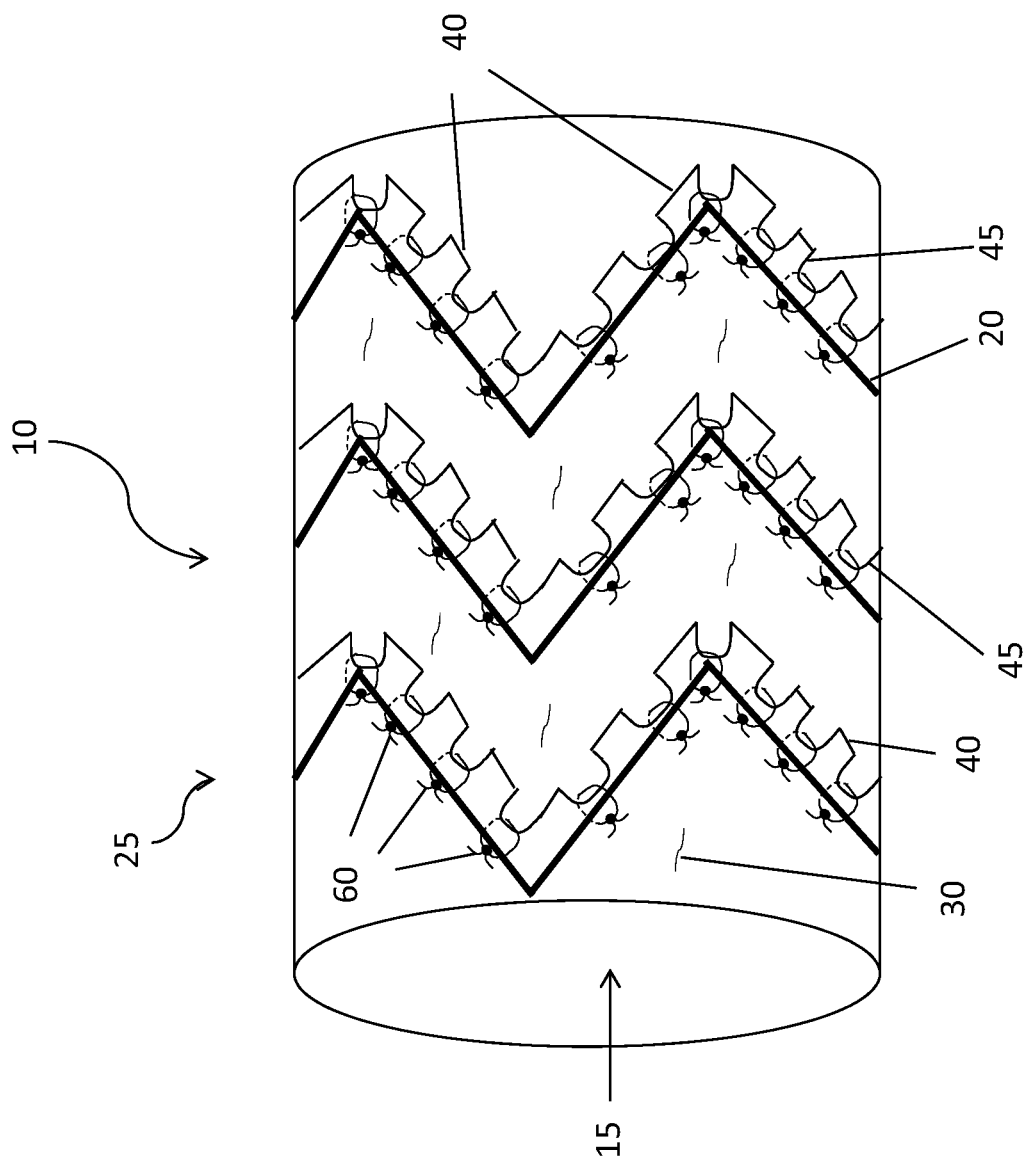
FIG. 1 is a view of one embodiment of the stent-graft of the invention where the stent wire is configured as a Z-type stent.

Referring now to FIG. 1, an illustration of one embodiment of a stent-graft 10 is shown. The stent 25 is formed from a first stent wire 20 configured into a stent wire pattern. The stent may also be fashioned from multiple wires. The exemplary stent wire pattern in FIG. 1 is a zigzag or Z-pattern (a "Z-stent" or a "Gianturco stent"). A Gianturco stent may comprise a series of substantially straight segments interconnected by a series of bent segments. The bent segments comprise acute bends or apices. The stent is arranged in a zigzag configuration in which the straight segments are set at angles relative to each other and are connected by the bent segments. The stent may comprise a variety of other configurations. For example, the stent may comprise a wire-mesh, coil or helical shape, or a slotted tube configuration.

Also shown in FIG. 1 is graft material 30 (the presence of fabric material is illustrated by wavy lines). The graft material is fashioned into a substantially tubular shape with an outer surface, an inner surface, and a lumen 15 extending through the graft. Sewn into the graft material 30 is a continuous anchoring machine stitching 40 where the machine stitching has loop points 45 at intervals along the machine stitching The loop points are disposed on the outer surface of the graft with the loop points projecting out from the surface of the graft material. The stent wire is attached to the graft at the loop points. The stent wire 20 is disposed around the graft material 30 and the machine stitching and the loop points follow/outline the stent wire pattern. FIG. 1 shows a graft with three rows of continuous machine stitching However, the graft of the invention may have any number of rows of continuous machine stitching that is appropriate for the particular application/size of the graft.

The stent is attached to the graft material in the embodiment of FIG. 1 by a plurality of discrete sutures 60 at loop points 45. The attachment by each discrete suture is at an independent loop point and the stent wire is attached to the graft material at each of the loop points. Thus, a point of attachment between the stent wire and a loop point is created at each loop point having a discrete suture. As called for by the particular application, in certain embodiments the stent may be attached to the graft material with a discrete suture at a plurality of loop points that represent fewer than all the loop points present in the machine stitching. In other embodiments, the stent is attached to the graft material by discrete sutures at all or substantially all of the loop points.

FIG. 2A illustrates the attachment of a segment of the stent wire 20 to the machine stitching 40 at the loop points 45 using discrete sutures 60. FIG. 2D illustrates an alternate embodiment showing that the loop points 47 may be shaped other than as shown in FIG. 1 and FIG. 2A. In general, the loop points may have any shape or size that permits the use of sutures to attach to the stent wire.

The attachment of the stent wire to the loop points (and hence to the graft material) may be by tying or knotting with the discrete sutures at the plurality of loop points. For example, the discrete sutures may be passed through the loop points and tied or knotted around the stent wire. Knots well known to those skilled in the art may be used such as, for example, a square knot or a surgeon's knot.

FIG. 2B shows an alternate embodiment where a discrete suture 62 attaches the stent wire 20 to the machine stitching 40 at more than one loop point 45. In FIG. 2B, the discrete suture 62 is tied at two adjacent loop points, looping over the stent wire 20. In an alternative embodiment to that shown in FIG. 2B, the suture 62 may form one or more complete 360° loops around the stent wire before tying to the second loop point. FIG. 2C illustrates yet another embodiment where suture 64 is tied to two non-adjacent loop points and passes through in intervening loop point. Although FIG. 2C shows the suture 64 as a running suture passing through a single intervening loop point, a suture may pass through a plurality of intervening loop points and around the stent wire without tying to the intervening loop points. A running suture may wrap around the stent wire and intervening loop point as in FIG. 2C without making a complete 360° loop around the wire or loop point. In other embodiments, the running suture may make one or more complete 360° loops around either the wire or loop point before continuing on to the next point of attachment. In other variations on the embodiments described above, the suture may be tied or knotted around the stent wire rather than just looping over or around the stent wire.

Figure 2E:
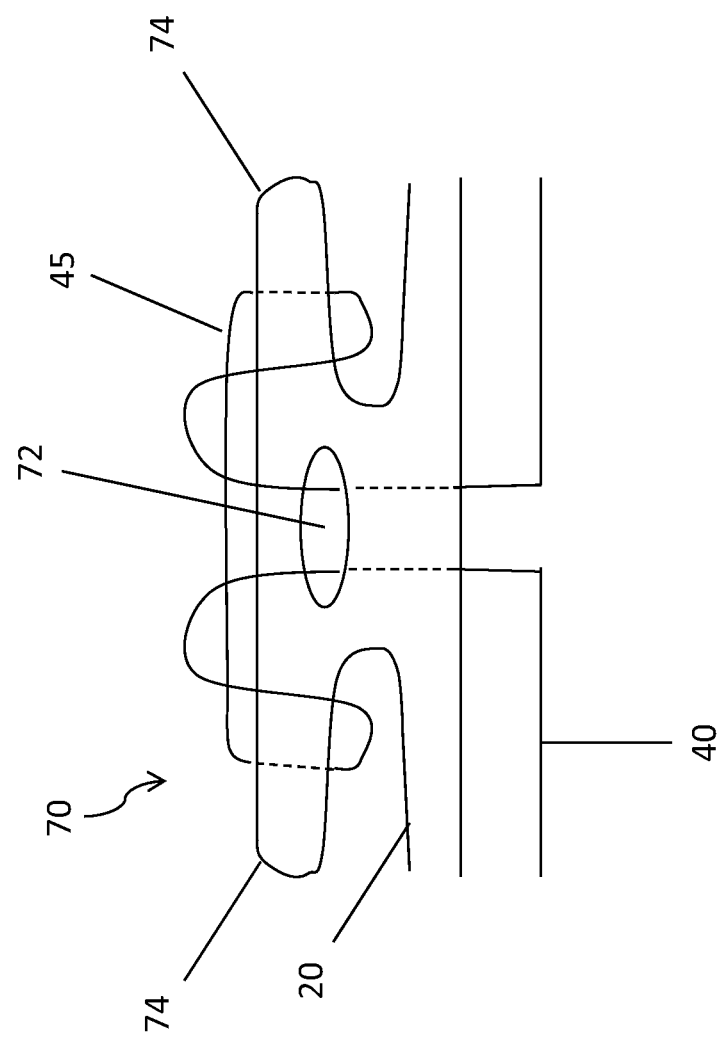

FIG. 2E illustrates yet another exemplary embodiment of the attachment of a loop point to a stent strut. The stent strut in FIG. 2E includes a hook point 70 afixed to a stent strut. Hook point 70 has an aperture 72 and horns 74. In FIG. 2E. the loop point 45 is threaded through the aperature 72, opened, pulled around horns 74 and locked in place around the hook point 70. The design of the hook point in FIG. 2E is merely exemplary as a variety of shapes and sizes of stent protrusions may be used to hook loop points 45 to a stent strut in order to attach a graft to a stent.

The embodiments shown in the Figures and described herein illustrate the points of attachment with a single suture at one or more loop points. For greater strength of attachment, however, multiple sutures may also be used per loop point. Alternatively, multiple sutures may overlap where the sutures attach at more than one loop point.

Figure 3A:
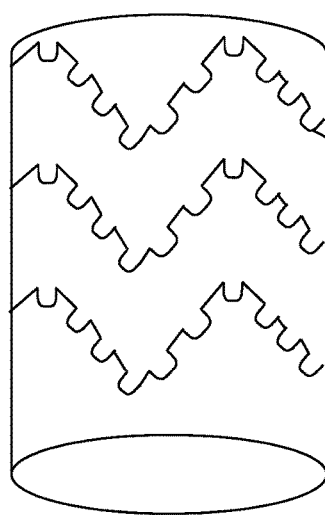
FIGS. 3A-3D illustrate the steps of manufacturing an exemplary stent-graft embodiment having a zigzag stent wire pattern.
Figure 3B:
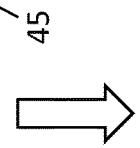
Figure 3B:
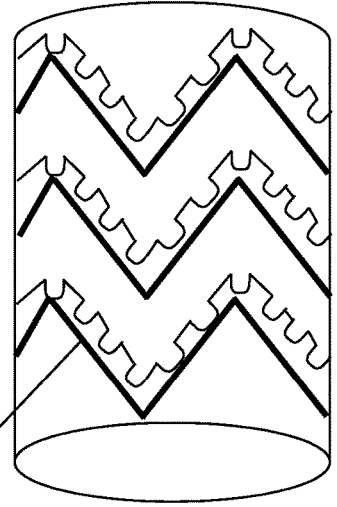
Figure 3C:
Figure 3C:
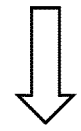
Figure 3C:
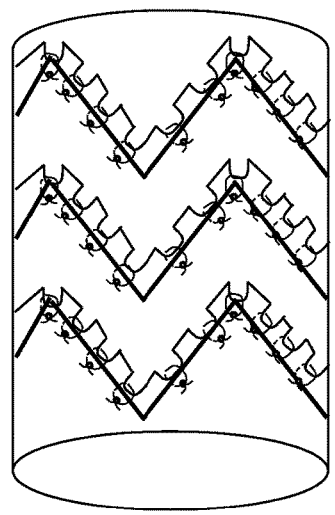
Figure 3D:
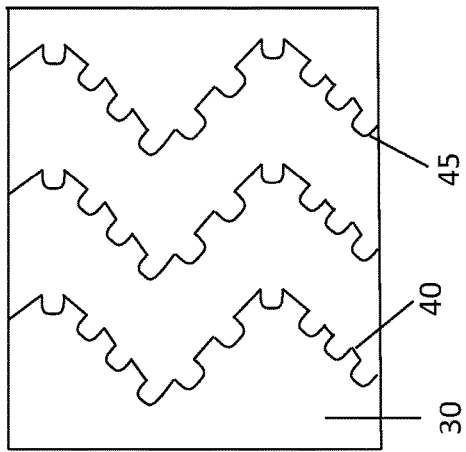

FIGS. 3A-3D illustrate exemplary steps of manufacturing one embodiment of the stent-graft of the invention where the stent is a Z-stent. The method involves first creating a continuous anchoring machine stitching 40 with a plurality of loop points 45 on the graft fabric in a stent wire pattern as shown in FIG. 3A. In one embodiment, a flat sheet of fabric is laid out on an embroidering machine and the machine runs a machine stitch with loop points along the pathway of the stent wire. In certain embodiments, a thread color different than the fabric is used in the machine stitching to allow visualization of where the stents will be placed on the final device. Once the machine stitching is completed, the flat sheet is tailored into the desired shape. FIG. 3B shows the graft material fashioned into a tubular shape, although other shapes are possible such as a bifurcated. The machine stitch is created such that the loop points 45 are on the external surface of the graft. The stent is then placed on the graft material and the stent wires 20 aligned with the machine stitching as illustrated in FIG. 3C. The stent-graft in FIG. 3D is completed by tack stitching the stent wires 20 to the machine stitch with discrete sutures 60 (shown in greater detail in FIGS. 1-2D). The sutures are looped through the machine stitching at the loop points creating a plurality of attachment points between the machine stitching (and hence the graft material) and the stent wire. This final step may be carried out using conventional hand-stitching techniques.

The present invention provides several advantages over conventional methods of hand-stitching a stent to a graft. The machine stitch can be made using a smaller needle than could be used with hand-stitching techniques. This minimizes the hole size created in the fabric during the stitching and thus reduces the risk of leakage through holes in the graft material. Machine stitching is also more efficient and faster than hand-stitching thereby reducing the cost of manufacturing stent-grafts. Machine stitching also reduces errors in the stent attachment location in that the machine is defining where the attachment of the stent is made versus having a sewer decide where to poke the needle through the fabric. The pre-sewn anchoring stitch also eliminates the need for drawing or marking on the fabric, thereby avoiding the potential for contamination or damage to the graft fabric.

In some embodiments, a stent may include a single flange, two asymmetrically shaped flanges, or may entirely lack flanges and instead have a uniform or substantially uniform lumen diameter along the entire length of the stent. In some embodiments, a stent may comprise a proximal tube portion, a distal tube portion, a central tube portion disposed between the proximal tube portion and the distal tube portion, such that the stent forms a continuous structure having a substantially uniform inner diameter and outer diameter throughout. A stent may include a uniform lumen diameter along the length of the stent but include slightly flared proximal and/or distal ends. The central body portion may smoothly transition to a flange or flare, or alternatively, may progressively step up in lumen diameter to a flange or flare.

Generally, a stent may be implanted in a vessel (e.g., esophagus, duodenum, colon, trachea, or the like) such that the central body portion engages a diseased area and the flanges or ends engage healthy tissue adjacent the diseased area. Preferably, the flanges are configured to anchor the stent at the site of implantation, thereby reducing the incidence of antegrade and retrograde migration. Preferably, the flanges are sized and shaped to accommodate the vessel or organ of implantation. For example, stents destined for lower esophageal implantation may have differently shaped and sized flanges compared to a stent designed for upper esophageal implantation. Further, the flanges may be atraumatically shaped to reduce incidence of tissue perforation and overgrowth. For example, the absolute ends of the flanges may curve or bend inward toward the stent lumen to minimize tissue damage at or near the stent ends. In certain embodiments, a stent may include other design elements configured to secure the stent at the site of implantation. For example, in certain embodiments, a stent may include anchors, hooks, or barbs that will anchor the stent to the internal wall of the targeted body lumen. In other embodiments, the stent may be sutured to the site of implantation at one or more portions of the stent structure.

In some embodiments, a stent may include one or more components configured to aid in visualization and/or adjustment of the stent during implantation, repositioning, or retrieval. For example, a stent may include one or more radiopaque markers configured to provide for fluoroscopic visualization for accurate deployment and positioning. Radiopaque markers may be affixed (e.g., by welding, gluing, suturing, or the like) at or near the ends of the stent at a cross point of the wire. In some embodiments, a stent may include four radiopaque markers with two markers affixed to a first flange and two to a second flange. Optionally, radiopacity may be added to a stent through covering (also referred to as coating) processes such as sputtering, plating, or co-drawing gold or similar heavy metals onto the stent. Radiopacity may also be included by alloy addition. Radiopaque materials and markers may be comprised of any suitable biocompatible materials, such as tungsten, tantalum, molybdenum, platinum, gold, zirconium oxide, barium salt, bismuth salt, hafnium, and/or bismuth subcarbonate. Additional methods are contemplated, including but not limited to, use of palladium or a nitinol wire with a platinum core, such as the DFT® wire available from Fort Wayne Metals, Fort Wayne, Ind.

In some embodiments, a stent may include one or more loops, lassos, or sutures on the stent structure to facilitate repositioning or removal of the stent during or after implantation. For example, a stent may include a loop at or near the proximal end of the stent. The loop material may circumscribe the flange and in certain embodiments may be wound through the absolute end cells to affix the loop to the stent. The loop may comprise any appropriate biocompatible materials, such as for example, stainless steel, suture materials or other polymeric materials such as polyethylene, ultra-high molecular weight polyethylene, polyester, nylon, or the like. Optionally, the lasso may be coated with a material, such as polytetrafluoroethylene, to reduce frictional interactions of the lasso with surrounding tissue.

A stent may be made from any suitable biocompatible material(s). For example, a stent may include materials such as shape memory alloys, stainless steel, nitinol, MP35N, gold, tantalum, platinum or platinum iridium, niobium, tungsten, Iconnel® (available from Special Metals Corporation, Huntington, W.V.), ceramic, nickel, titanium, stainless steel/titanium composite, cobalt, chromium, cobalt/chromium alloys, magnesium, aluminum, or other biocompatible metals and or composites or alloys. Examples of other materials that may be used to form stents include carbon or carbon fiber; cellulose acetate, cellulose nitrate, silicone, polyethylene terephthalate, polyurethane, polyamide, polyester, polyorthoester, polyanhydride, polyether sulfone, polycarbonate, polypropylene, ultra high molecular weight polyethylene, polytetrafluoroethylene, or another biocompatible polymeric material, or mixtures or copolymers of these; polylactic acid, polyglycolic acid or copolymers thereof; a polyanhydride, polycaprolactone, polyhydroxybutyrate valerate or another biodegradable polymer, or mixtures or copolymers of these; a protein, an extracellular matrix component, collagen, fibrin, or another biologic agent; or a suitable mixture of any of these.

Stents according to the present disclosure may be formed by any suitable method as is known in the art. In certain embodiments, stents may be fabricated by braiding, weaving, knitting, crocheting, welding, suturing, or otherwise machining together one or more filaments or wires into a tubular frame. Such stents may be referred to as braided, woven, or mesh stents. A braided stent may be fabricated by, for example, use of a braiding mandrel having specifically designed features (e.g., grooves and detents) for creating such a stent. A variety of braiding patterns are possible, such as for example, one-under and one-over patterns or two-under and two-over patterns. The filaments or wires may be of various cross-sectional shapes. For example, the filaments or wires may be flat in shape or may have a circular-shaped cross-section. The filaments or wires may have any suitable initial diameter, such as for example, from about 0.10 to about 0.30 mm.

In some embodiments, stents may be formed from metallic or polymeric sheets or tubular blanks. For example, a stent framework comprising a selected pattern of struts defining a plurality of cells or interstices may be fabricated by subjecting a metallic or polymeric sheet or tubular blank to laser cutting, chemical etching, high-pressure water etching, mechanical cutting, cold stamping, and/or electro discharge machining. After obtaining a sheet of cut, etched or machined material with the appropriate strut pattern, the sheet may be rolled into a tubular shape to form the stent framework. The stent framework may also be machined from a tubular blank, thereby eliminating the need for a rolling step.

Many different types of graft materials may be used. Common examples of graft materials currently used include expandable polytetrafluoroethylene (ePTFE), polytetrafluoroethylene (PTFE), high molecular weight polyethylene, Dacron, polyester, fabrics and collagen. However, graft materials may be made from numerous other materials as well, including both synthetic polymers and natural tissues, including small intestine submucosa (SIS). In one embodiment, the graft material has a weave density making it relatively impermeable to blood flow through the wall but still relatively thin in wall thickness (e.g., 0.08 to 1.2 mm).

The machine stitch and sutures may be made of any suitable biocompatible material that is preferably highly durable and wear resistant. Examples of suitable materials include synthetic fibers made from polyamides (nylon), polyolefins (polyethylene, polypropylene), polyesters (Dacron™), polybutesters, and high molecular weight polyethylene.

Those of skill in the art will appreciate that embodiments not expressly illustrated herein may be practiced within the scope of the present discovery, including that features described herein for different embodiments may be combined with each other and/or with currently-known or future-developed technologies while remaining within the scope of the claims presented here. It is therefore intended that the foregoing detailed description be regarded as illustrative rather than limiting. It is understood that the following claims, including all equivalents, are intended to define the spirit and scope of this discovery. Furthermore, the advantages described above are not necessarily the only advantages of the discovery, and it is not necessarily expected that all of the described advantages will be achieved with every embodiment of the discovery.

What is claimed is:

1. A stent-graft comprising:
   a first stent, the first stent comprising a first stent wire configured in a stent wire pattern;
   graft material, the graft material having a substantially tubular first graft shape with an inner surface and an outer surface and a lumen extending therethrough;
   a plurality of discrete sutures that follow the stent wire pattern; and
   a continuous machine stitch, stitched into the graft material and following the stent wire pattern and comprising a plurality of loop points, each loop point comprising a portion of the continuous machine stitch that projects from a surface of the graft material in a loop, wherein the plurality of loop points are disposed on the outer surface of the substantially tubular first graft shape and follow the stent wire pattern; and
   wherein the plurality of discrete sutures attach the first stent wire to the continuous machine stitch at the plurality of loop points on the outer surface of the substantially tubular first graft shape.

2. The stent-graft of claim 1 wherein each suture of the plurality of discrete sutures attaches the first stent wire to the continuous machine stitch at an independent loop point of the plurality of loop points.

3. The stent-graft of claim 1 wherein the first stent wire is attached to the continuous machine stitch at substantially all of the plurality of loop points.

4. The stent-graft of claim 2 wherein the first stent wire is attached to the continuous machine stitch at substantially all of the plurality of loop points.

5. The stent-graft of claim 1 wherein the stent wire pattern comprises a generally zig-zag shape.

6. The stent-graft of claim 1 wherein the plurality of discrete sutures ties the first stent wire to the continuous machine stitch with a knot at the plurality of loop points.

7. The stent graft of claim 1 wherein each suture of the plurality of discrete sutures ties the first stent wire to the continuous machine stitch with a knot at an independent loop point of the plurality of loop points.

8. The stent graft of claim 7 wherein the first stent wire is tied to the continuous machine stitch with a knot at substantially all of the plurality of loop points.

9. The stent-graft of claim 7 wherein each of the plurality of discrete sutures passes through the loop points and around the first stent wire.

10. The stent-graft of claim 8 wherein each of the plurality of discrete sutures passes through the loop points and around the first stent wire.

11. The stent-graft of claim 1 wherein at least one suture of the plurality of discrete sutures attaches the first stent wire to the continuous machine stitch at more than one loop point of the plurality of loop points.

12. The stent-graft of claim 11 wherein at least one suture of the plurality of discrete sutures ties the first stent wire to the continuous machine stitch at more than one loop point of the plurality of loop points.

13. The stent-graft of claim 11 wherein at least one suture of the plurality of discrete sutures attaches the first stent wire to the continuous machine stitch at a first loop point and a second loop point.

* * * * *